(12) United States Patent
Byrne et al.

(10) Patent No.: US 8,349,351 B2
(45) Date of Patent: *Jan. 8, 2013

(54) CONTACT DRUG DELIVERY SYSTEM

(75) Inventors: Mark E. Byrne, Auburn, AL (US);
Siddarth Venkatesh, Auburn, AL (US)

(73) Assignee: Auburn University, Auburn, AL (US)

( * ) Notice: Subject to any disclaimer, the term of this patent is extended or adjusted under 35 U.S.C. 154(b) by 421 days.

This patent is subject to a terminal disclaimer.

(21) Appl. No.: 11/346,770

(22) Filed: Feb. 3, 2006

(65) Prior Publication Data

US 2006/0177483 A1 Aug. 10, 2006
US 2010/0129424 A9 May 27, 2010

Related U.S. Application Data

(60) Provisional application No. 60/692,049, filed on Jun. 17, 2005, provisional application No. 60/736,140, filed on Nov. 10, 2005, provisional application No. 60/650,450, filed on Feb. 4, 2005.

(51) Int. Cl.
*A61K 9/00* (2006.01)

(52) U.S. Cl. ........................................ 424/429

(58) Field of Classification Search ........................ None
See application file for complete search history.

(56) References Cited

U.S. PATENT DOCUMENTS

| | | | |
|---|---|---|---|
| 4,668,506 A | 5/1987 | Bawa | |
| 4,775,531 A | 10/1988 | Gilbard | 424/128 |
| 4,911,933 A | 3/1990 | Gilbard | 424/663 |
| 4,931,279 A | 6/1990 | Bawa et al. | 424/427 |
| 5,318,780 A | 6/1994 | Viegas et al. | 424/427 |
| 5,587,175 A | 12/1996 | Viegas et al. | 424/427 |
| 5,840,338 A | 11/1998 | Roos et al. | 424/488 |
| 5,876,709 A | 3/1999 | Itoh et al. | 424/78.04 |
| 5,958,443 A | 9/1999 | Viegas et al. | 424/427 |
| 6,136,334 A | 10/2000 | Viegas et al. | 424/427 |
| 6,375,973 B2 | 4/2002 | Yanni | 424/427 |
| 6,552,103 B1 * | 4/2003 | Bertozzi et al. | 523/106 |
| 6,703,039 B2 | 3/2004 | Xia et al. | 424/427 |
| 6,730,065 B1 | 5/2004 | Horn | 604/294 |
| 6,735,470 B2 | 5/2004 | Henley et al. | 604/20 |
| 7,332,586 B2 | 2/2008 | Franzen et al. | |
| 2001/0006968 A1 * | 7/2001 | Trimming et al. | 514/254.07 |

(Continued)

FOREIGN PATENT DOCUMENTS

JP 62103029 A 5/1987

(Continued)

OTHER PUBLICATIONS

Machine translation of WO 03090805, May 2012.*

(Continued)

*Primary Examiner* — Paul Dickinson
(74) *Attorney, Agent, or Firm* — McKee, Voorhees & Sease, P.L.C.

(57) ABSTRACT

A drug delivery system is disclosed. The drug delivery system includes a recognitive polymeric hydrogel through which a drug is delivered by contacting biological tissue. The recognitive polymeric hydrogel is formed using a bio-template, which is a drug or is structurally similar to the drug, functionalized monomers, preferably having complexing sites, and cross-linking monomers, which are copolymerized using a suitable initiator. The complexing sites of the recognitive polymeric hydrogel that is formed preferably mimics receptor sites of a target biological tissue, biological recognition, or biological mechanism of action. The system in accordance with an embodiment of the intention is a contact lens for delivering a drug through contact with an eye.

10 Claims, 7 Drawing Sheets

U.S. PATENT DOCUMENTS

| | | | |
|---|---|---|---|
| 2004/0096477 A1 | 5/2004 | Chauhan et al. | |
| 2005/0163844 A1 | 7/2005 | Ashton | 424/468 |
| 2005/0208102 A1 | 9/2005 | Schultz | 424/427 |
| 2006/0100408 A1 | 5/2006 | Powell et al. | 526/320 |
| 2006/0177483 A1 | 8/2006 | Byrne et al. | 424/427 |

FOREIGN PATENT DOCUMENTS

| | | | |
|---|---|---|---|
| JP | 2004305313 A | 11/2004 | |
| JP | 2005314338 A | 11/2005 | |
| WO | 03090805 A1 | 11/2003 | |

OTHER PUBLICATIONS

Langer et al, Advances in biomaterials, drug delivery, and bionanotechnology, AIChE Journal, 2003, 49, 2990-3006.*

S. Venkatesh et al., Therapeutic Contact Lenses: A Biomimetic Approach Towards Tailored Ophthalmic Extended Delivery, Polymeric Materials: Science & Engineering 2006, 94, p. 766-767.

Siddarth Venkatesh et al., Biomimetic Recognitive Polymer Networks for Ocular Delivery of Anti-Histmines, Mater. Res. Soc. Symp. Proc. vol. 897E © 2006, p. 0897-J04-07.1 thru 0897-j04-07.6.

Siddarth Venkatesh et al., Ophthalmic Antihistamine Delivery Via Recognitive Contact Lenses for Allergic Relief, Aiche2005 Annvr. Meeting Proceedings, New York, NY, Inprogress 2005, p. 1-6.

Siddarth Venkatesh et al., A Biomimetic Approach Towards the Formation of Therapeutic Contact Lenses, Biomimetic & Biohybrid Materials, Biomedical Devices, and Drug Delivery Laboratories, Department of Chemical Engineering, Auburn University, Auburn, AL, USA 36849, 2006.

Siddarth Venkatesh et al., A Biomimetic Approach of Recognitive Contact Lenses for Tailored Loading-And Release of Antihistamines to Treat Allergic Rhinoconjunctivitis, Biomimetic & Biohybrid Materials, Biomedical Devices, and Drug Delivery Laboratories, Department of Chemical Engineering, Auburn University, Auburn, AL, USA 36849, 2006.

Mark E. Byrne et al., Molecular Imprinting within Hydrogels, Aug. 25, 2001, p. 149-161, Advanced Drug Delivery Reviews.

J. Zachary Hilt, Configurational Biomimesis in Drug Delivery: Molecular Imprinting of Biologically Significant Molecules, Jul. 28, 2004, 1599-1620, Advanced Drug Delivery Reviews.

Siddarth Venkatesh et al., Ophthalmic Antihistamine Delivery via Recognitive Contact Lenses for Allergic Relief, Biomimetic and Biohybrid Materials, Biomedical Devices, and Drug Delivery Laboratories, Department of Chemical Engineering, Auburn University, Auburn, AL 36849.

S. Venkatesh et al., "Applications of Biomimetic Systems in Drug Delivery", 2005 Ashley Publications, ISSN 1742-5247, pp. 1085-1096.

M. F. Saettone, "Progress and Problems in Ophthalmic Drug Delivery", Department of Bioorganic Chemistry and Biopharmaceutics, Business Briefing: Pharamatech 2002, pp. 1 of 6.

M. E. Byrne et al., "Networks for Recognition of Biomolecules: Molecular Imprinting and Micropatterning Poly(ethylene glycol)-Containing Films", Polym. Adv. Technol. 13, (2002), 798-816.

R. D. Schoenwald, "Ocular Pharmacokinetics", Chapter 9, 1997, pp. 119-138.

M. E. Byrne et al., "Molecular Imprinting Within Hydrogels", Advanced Drug Delivery Reviews, 56, 1599-1620, 2004.

Alvarez-Lorenzo et al., "Soft Contact Lenses Capable of Sustained Delivery of Timolol," J. Pharmaceutical Sciences, vol. 91, No. 10, Oct. 2002, pp. 2182-2192.

Hiratani et al., "Timolol uptake and release by imprinted soft contact lenses made of N,N-diethylacrylamide and methacrylic acid," J. Controlled Release, 83 (2002) 223-230.

Hiratani et al., "The nature of backbone monomers determines the performance of imprinted soft contact lenses as timolol drug delivery systems," Biomaterials 25 (2004) 1105-1113.

English Abstract of WO03090805 (A1), Menicon Co Ltd, published Nov. 6, 2003 (1 page).

English Abstract of JP2004305313 (A), Seed Co Ltd, published Nov. 4, 2004 (1 page).

English Abstract of JP2005314338 (A), Menicon Co Ltd, published Nov. 10, 2005 (1 page).

* cited by examiner

Aspartic Acid    Acrylic Acid

Asparagine    Acrylamide

Tyrosine    N-vinyl pyrrolidinone

CONTACT DRUG DELIVERY SYSTEM

RELATED APPLICATIONS

This application claims the priority under 35 U.S.C. §119 (e) of the co-pending U.S. Provisional Application Ser. No. 60/692,049, titled Sustained Ophthalmic Drug Delivery Via Biomimetic Recognitive Contact Lens", filed Jun. 17, 2005, the U.S. Provisional Application Ser. No. 60/736,140, titled "Sustained Ophthalmic Drug Delivery Via Biomimetic Recognitive Contact Lens", filed Nov. 10, 2005, and the U.S. Provisional Application Ser. No. 60/650,450, titled "Enhanced Loading and Extended Release Contact Lens for Histamine Antagonist Drug Ketotifen", filed Feb. 4, 2005, all of which are hereby incorporated by reference.

FIELD OF THE INVENTION

The invention relates to drug delivery systems. More specifically, this invention relates to systems for and method of time released ophthalmic drug delivery using contact lenses.

BACKGROUND OF THE INVENTION

Delivering medications via contact lenses has been a prevailing notion since the inception of using hydrophilic, crosslinked polymer gels on the surface of the eye. In fact, the first patent in the field from Otto Wichterle in 1965 states that "bacteriostatic, bacteriocidal or otherwise medicinally active substances such as antibiotics may be dissolved in the aqueous constituent of the hydrogels to provide medication over an extended period, via diffusion." However, there is evidence that this notion of a dissolved component in an aqueous constituent has been around for a much longer period of time. Evidence exists that honey soaked linen was used in ancient Rome as an ophthalmic dressing in the treatment of disease.

The biggest obstacle to using the fluid entrained in the aqueous portion of the polymer gel is maintaining a significant concentration of drug within the fluid to have a therapeutically relevant effect, which is ultimately limited by the solubility of the drug. This has been the primary reason why drug release from contact lenses has not become a clinical or commercial success. To an equivalent extent, the control over the drug delivery profile and an extended release profile is also important to therapeutic success and has not been demonstrated using these methods. Drug uptake and release by conventional (i.e., currently available) soft contact lenses can lead to a moderate intraocular concentration of drug for a very short period of time, but does not work very well due to a lack of sufficient drug loading and poor control of release. The use of soft, biomimetic contact lens carriers (i.e., recognitive polymeric hydrogels) described herein has the potential to greatly enhance ocular drug delivery by providing a significant designed and tailorable increase in drug loading within the carrier as well as prolonged and sustained release with increased bioavailability, less irritation to ocular tissue, as well as reduced ocular and systemic side effects.

The ocular bioavailability of drugs applied to the eye is very poor (i.e., typically less than 1-7% of the applied drug results in absorption with the rest entering the systemic circulation). Factors such as ocular protective mechanisms, nasolacrimal drainage, spillage from the eye, lacrimation and tear turnover, metabolic degradation, and non-productive adsorption/absorption, etc., lead to poor drug absorption in the eye. Currently, more efficient ocular delivery rests on enhancing drug bioavailability by extending delivery and/or by increasing drug transport through ocular barriers (e.g., the cornea—a transparent, dome-shaped window covering the front of the eye; the sclera—the tough, opaque, white of the eye; and the conjunctiva—a mucous membrane of the eye with a highly vascularized stroma that covers the visible part of the sclera). A topically applied drug to the eye is dispersed in the tear film and can be removed by several mechanisms such as:

(i) irritation caused by the topical application, delivery vehicle, or drug which induces lacrimation leading to dilution of drug, drainage, and drug loss via the nasolacrimal system into the nasopharynx and systemic circulation (e.g., the rate drainage increases with volume);

(ii) normal lacrimation and lacrimal tear turnover (16% of tear volume per minute in humans under normal conditions);

(iii) metabolic degradation of the drug in the tear film;

(iv) corneal absorption of the drug and transport;

(v) conjunctival absorption of the drug and scleral transport;

(vi) conjunctival 'non-productive' absorption via the highly vascularized stroma leading to the systemic circulation; and (vii) eyelid vessel absorption leading to systemic circulation.

Therefore, due to these mechanisms, a relatively low proportion of the drug reaches anterior chamber ocular tissue via productive routes such as mechanisms (iv) and (v).

For posterior eye tissue and back of the eye diseases (e.g., age-related macular degeneration, retinal degeneration, diabetic retinopathy, glaucoma, retinitis pigmentosa, etc.), the amount of drug delivered can be much less compared to front of the eye disease. To treat back of the eye disease, four approaches have typically been used, topical, oral (systemic delivery), intraocular, and periocular delivery.

Topically applied drugs diffuse through the tear film, cornea/sclera, iris, ciliary body, and vitreous before reaching posterior tissues, but due to the added transport resistances do not typically lead to therapeutically relevant drug concentrations. However, researchers have shown that topically applied drugs do permeate through the sclera by blocking corneal absorption and transport. Intravitreal injections (injections into the eye) require repeated injections and have potential side effects (hemorrhage, retinal detachment, cataract, etc.) along with low patient compliance. Extended release devices have been used but require intraocular surgery and often have the same incidence of side effects. Periocular drug delivery is less invasive and also requires injections or implant placement for predominantly transscleral delivery.

To overcome most of these protective mechanisms, topical formulations have remained effective by the administration of very high concentrations of drug multiple times on a daily basis. For a number of drugs high concentrations can lead to negative effects such as burning, itching sensations, gritty feelings, etc., upon exposure of the medication to the surface of the eye as well as increased toxicity and increased ocular and systemic side effects. However, traditional ophthalmic dosage forms such as solutions, suspensions, and ointments account for 90% of commercially available formulations on the market today. Solutions and suspensions (for less water soluble drugs) are most commonly used due to the ease of production and the ability to filter and easily sterilize. Ointments are used to much lesser extent due to vision blurring, difficulty in applying to the ocular surface, and greasiness. The term "eye drops" herein is meant to refer to all topological medications administered to a surface of the eye including but not limited to solutions, suspensions, ointments and combination thereof. In addition to the aforementioned problems, drug delivery through the use of eye drops does not provide for controlled time release of the drug. Eye drops medications typically have a low residence time of the drug on the surface of the eye.

The efficacy of topical solutions has been improved by viscosity enhancers that increase the residence time of drugs on the surface of the eye, which ultimately lead to increased bioavailability as well as more comfortable formulations. Also, inclusion complexes have been used for poorly soluble drugs, which increase solubility without affecting permeation.

Other recent delivery methods have included in situ gel-forming systems, corneal penetration or permeation enhancers, conjunctival muco-adhesive polymers, liposomes, and ocular inserts.

Ocular inserts, in some cases, achieve a relatively stable or constant, extended release of drug. For example, ocular inserts such as Ocusert® (Alza Corp., FDA approved in 1974) consist of a small wafer of drug reservoir enclosed by two ethylene-vinyl acetate copolymer membranes, which is placed in the corner of the eye and provides extended release of a therapeutic agent for approximately 7 days (i.e., pilocarpine HCL, for glaucoma treatment reducing intraocular pressure of the eye by increasing fluid drainage). Lacrisert (Merck) is a cellulose based polymer insert used to treat dry eyes. However, inserts have not found widespread use due to occasional noticed or unnoticed expulsion from the eye, membrane rupture (with a burst of drug being released), increased price over conventional treatments, etc.

Mucoadhesive systems and in-situ forming polymers typically have problems involving the anchorage of the carrier as well as ocular irritation resulting in blinking and tear production. Penetration enhancers may cause transient irritation, alter normal protection mechanisms of the eye, and some agents can cause irreversible damage to the cornea.

The novel soft, biomimetic contact lens carriers proposed in this work will provide a significant increase in drug loading within the gel as well as prolonged and sustained release. This will lead to prolonged drug activity and increased bioavailability, reduced systemic absorption, reduced ocular and systemic side effects, and increased patient compliance due to reduced frequency of medication and reduced irregularity of administration (i.e., eye drop volume depends on angle, squeeze force, etc., and has been experimentally verified to be highly variable). They will also be able to be positioned easily as well as easily removed with or without use to correct vision impairment. Since they will be positioned on the cornea, this will lead to enhanced corneal permeability as well.

SUMMARY OF THE INVENTION

The present invention is directed to a drug delivery methods and systems. The drug delivery system includes a recognitive polymeric hydrogel through which a drug is delivered by contacting biological tissue. The recognitive polymeric hydrogel is formed using a bio-template, which is a drug or is structurally similar to the drug, functionalized monomers, preferably having complexing sites, and cross-linking monomers, which are copolymerized using a suitable initiator, such as described in detail below. The complexing sites of the recognitive polymeric hydrogel that is formed preferably mimics receptor sites of a target biological tissue, biological recognition, or biological mechanism of action. The system unitizes what is referred to herein as a biomimetic recognitive polymeric hydrogel.

The system in accordance with an embodiment, the system is an ophthalmic drug system. The ophthalmic drug system includes soft contact lenses formed from the biomimetic recognitive polymeric hydrogel and that are impregnated with a drug that can be release over a duration of time while in contact with eyes. The invention is directed to both corrective or refractive contact lenses and non-corrective or non-refractive contact lenses. While the invention as described herein refers primarily to ophthalmic drug systems, it is understood that the present invention has applications in a number of different contact drug delivery systems. For example, the biomimetic recognitive polymeric hydrogel can be used in bandages, dressings, and patch-type drug delivery systems to name a few.

In accordance with the embodiments of the invention a hydrogel matrix that is formed from silicon-based cross-linking monomers, carbon based or organic-based monomers, macromers or a combination thereof. Suitable cross-linking monomers include but are not limited to Polyethylene glycol (200) dimethacrylate (PEG200DMA), ethylene glycol dimethacrylate (EGDMA), tetraethyleneglycol dimethacrylate (TEGDMA), N,N'-Methylene-bis-acrylamide and polyethylene glycol (600) dimethacrylate (PEG600DMA). Suitable silicon-based cross-linking monomers can include tris (trimethylsiloxy)silyl propyl methacrylate (TRIS) and hydrophilic TRIS derivatives such as tris(trimethylsiloxy) silyl propyl vinyl carbamate (TPVC), tris(trimethylsiloxy) silyl propyl glycerol methacrylate (SIGMA), tris(trimethylsiloxy)silyl propyl methacryloxyethylcarbamate (TSMC); polydimethylsiloxane (PDMS) and PDMS derivatives, such as methacrylate end-capped fluoro-grafted PDMS crosslinker, a methacrylate end-capped urethane-siloxane copolymer crosslinker, a styrene-capped siloxane polymer containing polyethylene oxide and polypropylene oxide blocks; and siloxanes containing hydrophilic grafts or amino acid residue grafts, and siloxanes containing hydrophilic blocks or containing amino acid residue grafts. The molecular structure of these monomers can be altered chemically to contain moieties that match amino acid residues or other biological molecules. In cases where the above monomers, when polymerized with hydrophilic monomers, a solubilizing cosolvent may be used such as dimethylsulfoxide (DMSO), isopropanol, etc. or a protecting/deprotecting group strategy.

Crosslinking monomer amounts can be from (0.1 to 40%, moles crosslinking monomer/moles all monomers); Functional monomers, 99.9% to 60% (moles functional monomer/ moles all monomers) with varying relative portions of multiple functional monomers; initiator concentration ranging from 0.1 to 30 wt %; solvent concentration ranging from 0% to 50 wt % (but no solvent is preferred); monomer to bio-template ratio (M/T) ranging from 0.1 to 5,000, preferably 200 to 1,000, with 950 preferred for the ketotifen polymers presented herein, under an nitrogen or air environment (in air, the wt % of initiator should be increased above 10 wt %.

The ophthalmic drug delivery system also includes a bio-template, that is drug molecules, prodrugs, protein, amino acid, proteinic drug, oligopeptide, polypeptide, oligonucleotide, ribonucleic acid, deoxyribonucleic acid, antibody, vitamin, or other biologically active compound. This also includes a drug with an attached bio-template. The bio-template is preferably bound to the hydrogel matrix through one or more of electrostatic interactions, hydrogen bonding, hydrophobic interactions, coordination complexation, and Van der Waals forces.

Bio-templates are preferably weakly bound to a hydrogel matrix through functionalized monomer units, macromer units or oligomer units that are co-polymerized into the hydrogel matrix to form receptor locations within the hydrogel matrix that resemble or mimic the receptor sites or molecules associated with the biological target tissue to be treated with the drug or the biological mechanism of action In accordance with the embodiments of the invention, a portion of the bio-template can be washed out from the recognitive hydrogel polymer, loaded with a drug. The polymerization reaction forms a contact lens. For example, the gel is polymerized in a mold or compression casting. After contact lenses are formed they can be used to administer the drug through contact with eyes. Alternatively, the recognitive hydrogel polymer can be formed into contact lenses, washed to remove a portion of the bio-template and then loaded with the drug. Where the bio-template is the drug, the washing step can be illuminated or truncated. In formulations where the bio-template is a drug, the free base form of the drug or hydrochloride salt of the drug can be used.

In accordance with the method of the present invention, a biomimetic recognitive polymeric hydrogel is formed by making a mixture or solution that includes amounts of a bio-template or drug, functionalized monomer or monomers, cross-linking monomer or monomers and polymerization initiator in a suitable solvent or without solvent. Suitable initiators include water and non-water soluble initiators, but are not limited to azobisisobutyronitrile (AIBN), 2,2-dimethoxy-2-phenyl acetophenone (DMPA), 1-hydroxycyclohexyl phenyl ketone (Irgacure® 184), 2,2-dimethoxy-1,2-diphenylethan-1-one (Irgacure 651), ammonium persulfate, iniferter such as tetraethylthiuram disulfide, or combinations thereof. The polymerization can be photo-initiated, thermally-initiated, redox-initiated or a combinations thereof.

The functionalized monomer or monomers complex with the bio-template and copolymerize with cross-linking monomer or monomers to form a biomimetic recognitive polymeric hydrogel, such as described above. Functional or reactive monomers useful herein are those which possess chemical or thermodynamic compatibility with a desired bio-template. As used herein, the term functional monomer includes moieties or chemical compounds in which there is at least one double bond group that can be incorporated into a growing polymer chain by chemical reaction and one end that has functionality that will interact with the bio-template through one or more of electrostatic interactions, hydrogen bonding, hydrophobic interactions, coordination complexation, and Van der Waals forces. Functional monomers includes macromers, oligomers, and polymer chains with pendent functionality and which have the capability of being crosslinked to create the recognitive hydrogel. Crosslinking monomer includes chemicals with multiple double bond functionality that can be polymerized into a polymer network. Examples of functionalized monomers include, but are not limited to, 2-hydroxyethylmethacrylate (HEMA), Acrylic Acid (AA), Acrylamide (AM), N-vinyl 2-pyrrolidone (NVP), 1-vinyl-2-pyrrolidone (VP), methyl methacrylate (MMA), methacrylic acid (MAA), acetone acrylamide, 2-ethyl-2-(hydroxymethyl)-1,3-propanediol trimethacrylate, N-(1,1-dimethyl-3-oxobutyl)acrylamide, 2-ethyl-2-(hydroxymethyl)-1,3-propanediol trimethacrylate, 2,3-dihydroxypropyl methacrylate, allyl methacrylate, 3-[3,3,5,5,5-pentamethyl-1,1-bis[pentamethyldisiloxanyl)oxy]trisiloxanyl]propyl methacrylate, 3-[3,3,3-trimethyl-1,1-bis(trimethylsiloxy) disiloxanyl]propyl methacrylate (TRIS), N-(1,1-dimethyl-3-oxybutyl)acrylamide, dimethyl itaconate, 2,2,2,-trifluoro-1-(trifluoromethyl)ethyl methacrylate, 2,2,2-trifluroethyl methacrylate, methacryloxypropylbis(trimethylsiloxy)methylsilane, methacryloxypropylpentamethyldisiloxane, (3-methacryloxy-2-hydroxypropyloxy)propylbis(trimethylsiloxy)methylsilane, 4-t-butyl-2-hydroxycyclohexyl methacrylate, dimethylacrylamide and glycerol methacrylate.

Once formed the biomimetic recognitive polymeric hydrogel can be formed into contact lenses or as described above the polymerization reaction forms the contact lenses.

In accordance with further embodiments of the invention, functionalized monomers are synthesized or selected by identifying receptor sites or molecules associated with the target biological tissue to be treated by the drug or that are associated with metabolizing the drug. Then functionalized portions of the functionalized monomers are synthesized to chemically and/or structurally resemble or mimic the receptor sites or molecules that are associated with the biological mechanism of action of the drug. These functionalized monomers are then copolymerized with the cross-linking monomer or monomers used to form the hydrogel matrix, such as described above.

After the drug has been depleted from the contact lenses through the eyes, the contact lenses can be re-loaded with the drug by soaking the contact lenses in the reconstituting drug solution. While the contact lense have been described in detail as being used to deliver antihistamines and other allergy drugs, ophthalmic drug delivery systems and methods of the present invention can be used to deliver any number of drugs through contact on the eye and/or systemically.

Drugs that can be delivered by the system and method of the present invention include, but are not limited to, Anti-bacterials Anti-infectives and Anti-microbial Agents (genteelly referred to as antibiotics) such as Penicillins (including Aminopenicillins and/or penicillinas in conjunction with penicillinase inhibitor), Cephalosporins (and the closely related cephamycins and carbapenems), Fluoroquinolones, Tetracyclines, Macrolides, Aminoglycosides. Specific examples include, but are not limited to, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate and bacitracin.

The ophthalmic drug delivery system and method of the present invention can also be used to deliver Non-steroidal (NSAIDs) and Steroidal Anti-inflammatory Agents (genteelly referred to as anti-inflammatory agents) including both COX-1 and COX-2 inhibitors. Examples include, but are not limited to, corticosteroids, medrysone, prednisolone, prednisolone acetate, prednisolone sodium phosphate, fluormetholone, dexamethasone, dexamethasone sodium phosphate, betamethasone, fluoromethasone, antazoline, fluorometholone acetate, rimexolone, loteprednol etabonate, diclofenac (diclofenac sodium), ketorolac, ketorolac tromethamine, hydrocortisone, bromfenac, flurbiprofen, antazoline and xylometazoline.

The ophthalmic drug delivery system and method of the present invention can also be used to deliver Anti-histamines, Mast cell stabilizers, and Anti-allergy Agents (generally referred to as anti-histamines). Examples include, but are not limited, cromolyn sodium, lodoxamide tromethamine, olopatadine HCl, nedocromil sodium, ketotifen fumarate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid and amlexanox.

In yet further embodiments of the invention the ophthalmic drug delivery system and method are used to deliver Antiviral Agents including, but not limited to, trifluridine and vidarabine; Anti-Cancer Therapeutics including, but not limited to, dexamethasone and 5-fluorouracil (5FU); Local Anesthetics including, but are not limited to, tetracaine, proparacaine HCL and benoxinate HCL; Cycloplegics and Mydriatics including, but not limited to, Atropine sulfate, phenylephrine HCL, Cyclopentolate HCL, scopolamine HBr, homatropine HBr, tropicamide and hydroxyamphetamine Hbr; Comfort Molecules or Molecules (generally referred as lubricating agents) to treat Keratoconjunctivitis Sicca (Dry Eye) including, but not limited to, Hyaluronic acid or hyaluronan (of varying Molecular Weight, MW), hydroxypropyl cellulose (of varying MW), gefarnate, hydroxyeicosatetranenoic acid (15-(S)-HETE), phospholipid-HETE derivatives, phoshoroylcholine or other polar lipids, carboxymethyl cellulose (of varying MW), polyethylene glycol (of varying MW), polyvinyl alcohol (of varying MW), rebamipide, pimecrolimus, ecabet sodium and hydrophilic polymers; Immunosuppressive and Immuno-modulating Agents including, but not limited to, Cyclosporine, tacrolimus, anti-IgE and cytokine antagonists; and Anti-Glaucoma Agents including beta blockers, pilocarpine, direct-acting miotics, prostagladins, alpha adrenergic agonists, carbonic anhydrase inhibitors including, but not limited to betaxolol HCL, levobunolol HCL, metipranolol HCL, timolol maleate or hemihydrate, carteolol HCL, carbachol, pilocarpine HCL, latanoprost, bimatoprost, travoprost, brimonidine tartrate, apraclonidine HCL, brinzolamide and dorzolamide HCL; decongestants, vasodilaters vasoconstrictors including, but not limited to epinephrine and pseudoephedrine

DETAILED DESCRIPTION OF A PREFERRED EMBODIMENT

Figure 1:
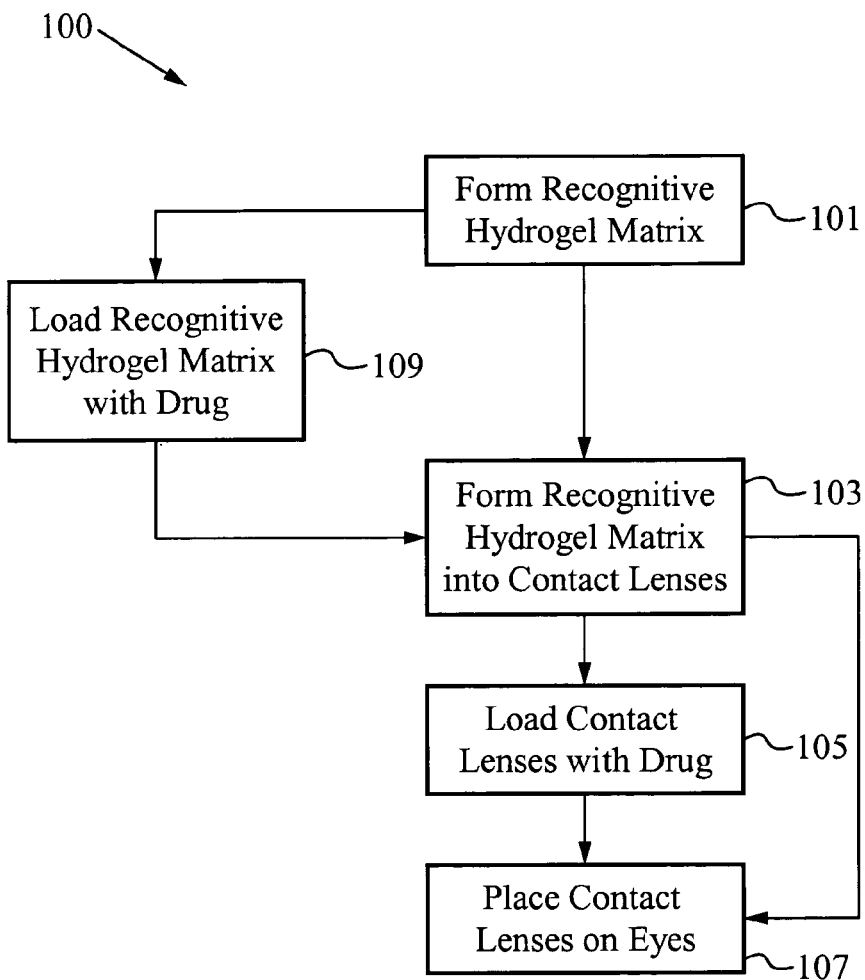
FIG. 1 is a block diagram showing the steps for making contact lenses, in accordance with the embodiments of the invention.

Hydrogels are insoluble, cross-linked polymer network structures composed of hydrophilic homo- or hetero-co-polymers, which have the ability to absorb significant amounts of water. Consequently, this is an essential property to achieve an immunotolerant surface and matrix (i.e., with respect to protein adsorption or cell adhesion). Due to their significant water content, hydrogels also possess a degree of flexibility very similar to natural tissue, which minimizes potential irritation to surrounding membranes and tissues.

The hydrophilic and hydrophobic balance of a gel carrier can be altered to provide tunable contributions that present different solvent diffusion characteristics, which in turn influence the diffusive release of a drug contained within the gel matrix. In general, one may polymerize a hydrophilic monomer with other less hydrophilic or more hydrophobic monomers to achieve desired swelling properties.

These techniques have led to a wide range of swellable hydrogels. Knowledge of the swelling characteristics is of major importance in biomedical and pharmaceutical applications since the equilibrium degree of swelling influences the diffusion coefficient through the hydrogel, surface properties and surface mobility, mechanical properties, and optical properties. Drug release depends on two simultaneous rate processes: water migration into the network and drug diffusion outward through the swollen gel.

Soft contact lenses are made of hydrogels. The typical material properties for contact lenses involve a number of considerations such as optical quality (good transmission of visible light), high chemical and mechanical stability, manufacturability at reasonable cost, high oxygen transmissibility, tear film wettability for comfort, and resistance to accumulation of protein and lipid deposits, as well as a suitable cleaning and disinfecting scheme.

Soft contact lenses typically consist of poly(2-hydroxyethyl methacrylate) (PHEMA). Other lens materials include HEMA copolymerized with other monomers such as methacrylic acid, acetone acrylamide, and vinyl pyrrolidone. Also, commonly used are copolymers of vinyl pyrrolidone and methyl methacrylate as well as copolymers of glycerol methacrylate and methyl methacrylate. Minor ingredients have included a variety of other monomers as well as cross-linking agents.

The immersion and soaking of soft contact lenses in drug solutions has shown promise in the increase of drug bioavailability with a minimization of side effects. However, the materials and constituent chemistry of the macromolecular chains and subsequent interaction with drugs is random and typically leads to poor drug loading.

In order to address the above referenced shortcomings, the present invention is directed to the use of biomimetic imprinting of hydrogels to make hydrogels matrices that can selectively bind a drug through complexing sites leading to improved loading of a drug and controlled time release of the drug. These hydrogels are referred to as recognitive polymeric hydrogels. The polymerization reaction forms the contact lenses, which can be used to administer drugs through contact with the eyes, thereby replacing traditional eye drop therapies. Alternatively, the recognitive polymeric hydrogels can be formed or fashioned into contact lenses which can be used to administer drugs through contact with the eyes, thereby replacing traditional eye drop therapies or other mechanisms of delivery.

For example, ketotifen fumurate is a potent fast acting and highly selective histamine H1 antagonists with a sustained duration of action. Levocabastine and ketotifen fumarate inhibits itching, redness, eyelid swelling, tearing, and chemosis induced by conjunctival provocation with allergens and histamine. With topical application in the form of eye drops, absorption is incomplete and bioavailability is low. Thus, the dose is usually administered multiple times daily. Also, due to a high concentration of drug and other constituents of the ophthalmic suspension preparation, patients are advised not to wear soft contact lenses. Accordingly, a soft contact lens that could be used to administer ketotifen fumurate would not only enhance the efficacy of the treatment, but also allow allergy sufferers to wear contact lenses.

Figure 2:
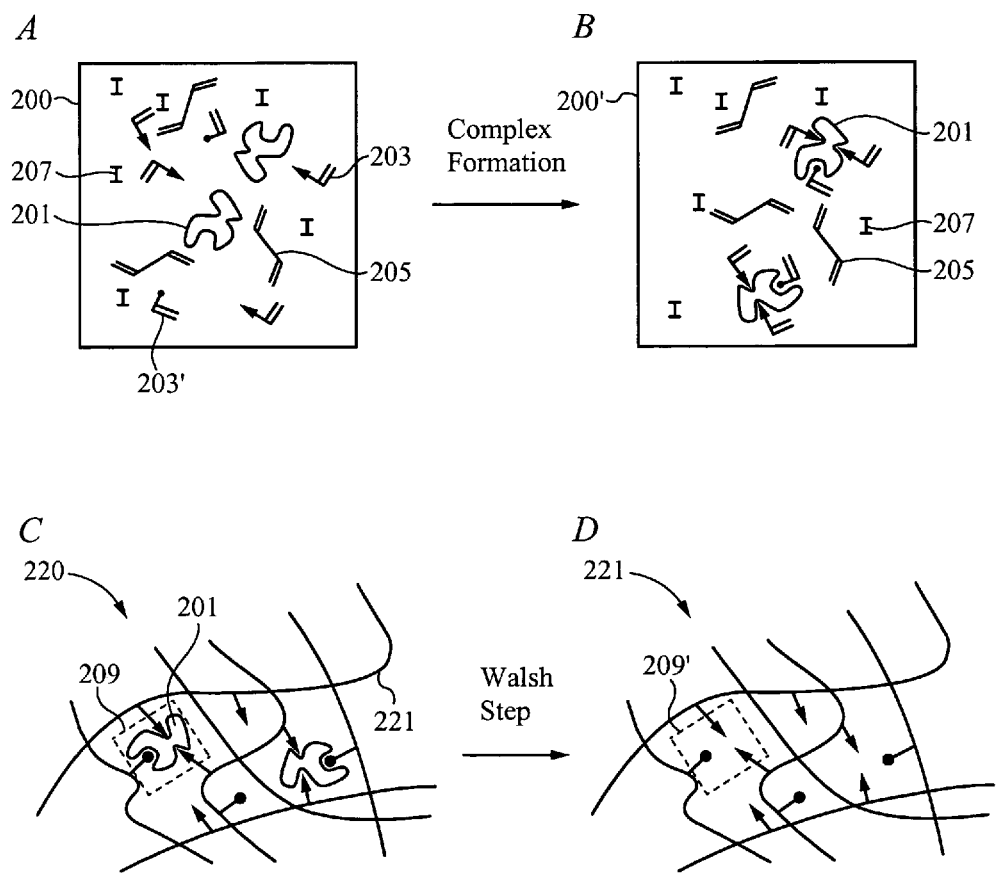
FIG. 2 illustrates the formation of a recognitive polymeric hydrogel, in accordance with the embodiments of the invention.

Referring to FIG. 1 which is a block diagram 100 outlining steps for making contact lenses, in accordance with the embodiments of the invention and FIG. 2 which is a graphical representation of forming a recognitive polymeric hydrogel 221. In the step 101, the recognitive hydrogel matrix 221 is formed. The recognitive hydrogel 221 is formed by generating a solution 200 comprising one or more bio-template 201, one or more functionalized monomers 203 and 203', one or more cross-linking monomers 205 with or without a solvent. In the solution 200' the functionalized monomers 203 and 203' complexes with the bio-templates 201. A suitable initiator or mixture initiators 207 is used to co-polymerize the functionalized monomers 203 and 203' with a cross-linking monomer 205 to form the loaded hydrogel 220 comprising a hydrogel matrix 221 with bio-templates 201 complexing at site 209 through the hydrogel matrix 221.

Preferably, the bio-templates are complexed with the hydrogel matrix 221 through weak or non-covalent interactions, as explained above, whereby the bio-templates can be washed or rinsed from the complexed hydrogel 220 to form an un-complexed recognitive polymeric hydrogel 221, which has vacant complexing sites 209 that can be used to complex drug molecules that are structurally and/or chemically similar to the bio-templates 201. It will be clear from the discussions above and below that the bio-templates can be a drug and, therefore, washing the bio-templates from the hydrogel matrix 221 may not be necessary for all drug delivery systems that are synthesized.

Still referring to both FIG. 1 and FIG. 2, after the recognitive hydrogel 221 is formed, in the step 101, in the step 103 the recognitive hydrogel 221 can be formed into contact lenses using any technique known in the art. Its is understood that the step the step 103 is not necessary, when the polymerization reaction forms the contact lenses, such as described previously. Where the bio-template is a drug, the contact lenses can be placed in contact with eyes in the step 107 to administer or deliver the drug to or through the eyes. Where, the bio-template 201 has been washed from the recognitive hydrogel matrix prior to or after the step 103 of forming the contact lenses from the recognitive hydrogel matrix, then in the step 109 or the step 105, respectively, the recognitive hydrogel matrix or the contact lenses are loaded with a drug. The recognitive hydrogel matrix or the contact lenses can be loaded with the drug by soaking the recognitive hydrogel matrix or the contact lenses in an aqueous drug solution.

Figure 3:
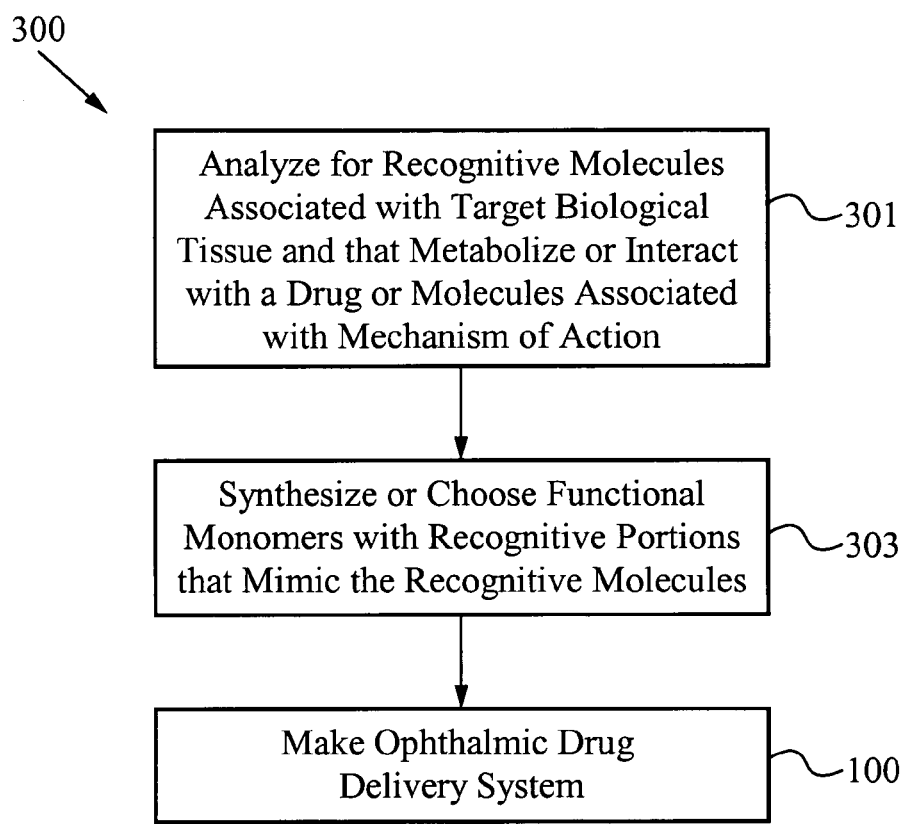
FIG. 3 illustrates a block diagram outlining steps for making funtionalized monomer used in the synthesis of recognitive polymeric hydrogels, in accordance with the embodiments of the invention.

Now referring to FIG. 2 and FIG. 3. In accordance with further embodiments of the invention prior to the step of making an ophthalmic drug delivery system, such as described with reference to FIG. 1, in the step 301 the target tissue to be treated with the drug or biological mechanism of action is studied to determine the types of molecules or functional groups that are associated with the action of the drug at the target tissue to effect the target tissue. Based on this information, in the step 303, funtionalized monomers are synthesized with functional groups that mimic or resemble molecules or functional groups that are associated with the action of the drug at the target tissue. The functionalized monomers with the functional groups that mimic or resemble molecules or functional groups that are associated with metabolizing the drug at the target tissue are then used to synthesize a drug delivery system, such as described above with reference to FIG. 1. The biomimetic approach is the processes of mimicking biological recognition or exploiting biological mechanisms. Specifically, it is the process of coordinating biological molecular recognition, interactions, or actions to design materials that can be structurally similar to and/or function in similar ways as biological structures.

Figure 4A:
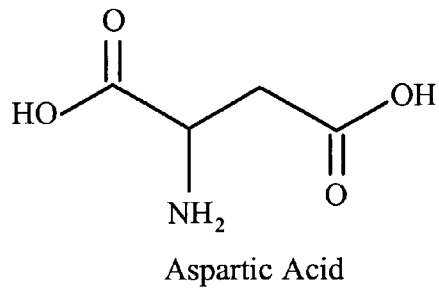
FIGS. 4A-C illustrate examples of sets of molecules that match, resemble or mimic each other.
Figure 4A:
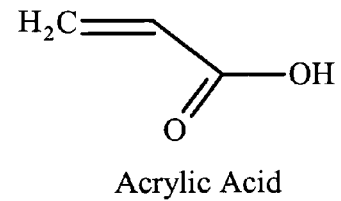
Figure 4B:
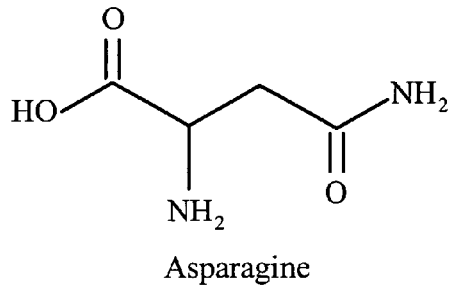
Figure 4B:
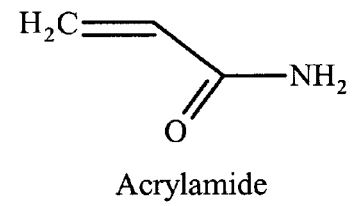
Figure 4C:
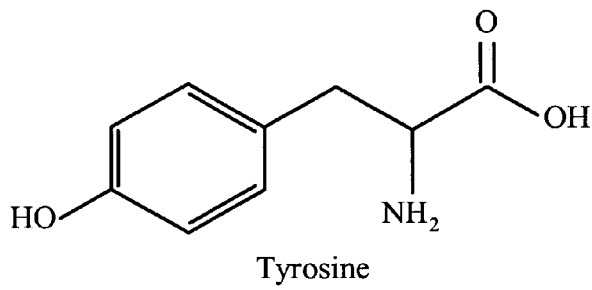
Figure 4C:
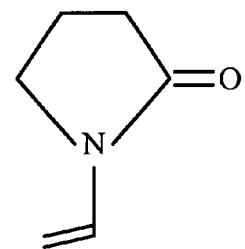

FIGS. 4A-C illustrate examples of sets of molecules that match, resemble or mimic each other. With reference to the bio-mimetic approach for synthesizing recognitive hydrogel polymers described above, acrylic acid can be used to mimic aspartic acid (FIG. 4A), acrylaminde can be used to mimic asparagine (FIG. 4B) and N-vinyl pyrrolidinone can be used to mimic tyrosine (FIG. 4C). Aspartic acid, asparagine, and tyrosine are known to be of the group of amino acids providing the non-covalent interactions in the ligand binding pocket for histamine. For example, structural analysis of ligand binding pockets and amino acids involved in multiple non-covalent binding points provide one of many rational frameworks to synthesize recognitive networks from functional monomers. Antihistamine has been shown to bind more tightly and have a higher affinity than histamine for the histamine binding pocket.

EXAMPLE

Materials and Methods: Acrylic Acid (AA), Acrylamide (AM), N-Vinyl-2-Pyrrolidone (NVP) and 2-hydroxyethylmethacrylate (HEMA), Azobisisobutyronitrile (AIBN), and Ketotifen Fumarate were purchased from Sigma-Aldrich. Polyethylene glycol (200) dimethacrylate (PEG200DMA) was purchased from Polysciences, Inc. All chemicals were used as received. Polymer and copolymer networks were made using various mixtures of above monomers (e.g. Poly (AA-co-AM-HEMA-PEG200DMA), Poly(AA-co-HEMA-co-PEG200DMA), Poly (AM-co-HEMA-co-PEG200DMA), Poly(AA-co-AM-co-NVP-co-HEMA-PEG200DMA)). Current work is directed to producing networks that can also be used in the formation of contact lens for anti-histamines with monomers and copolymers of molecules such as N-vinyl 2-pyrrolidone (NVP), 1-vinyl-2-pyrrolidone (VP), methyl methacrylate (MMA), methacrylic acid (MAA), acetone acrylamide, ethylene glycol dimethacrylate (EGDMA), 2-ethyl-2-(hydroxymethyl)-1,3-propanediol trimethacrylate, N-(1,1-dimethyl-3-oxobutyl) acrylamide, 2-ethyl-2-(hydroxymethyl)-1,3-propanediol trimethacrylate, 2,3-dihydroxypropyl methacrylate, allyl methacrylate any other suitable monomers, such as those referenced previously.

Accurate quantities of monomers, template molecules and crosslinkers were added in that order, and the mixture was sonicated to obtain a homogenous solution. In particular, a typical formulation consisted of 5 mole % cross-linking monomer (PEG200DMA) in a solution of Acrylamide (M), HEMA (M), Ketotifen (T), with an M/T ratio of approximately 950 (92% HEMA, 1% of remaining monomers, and approximately 1 mole % drug depending on the M/T ratio). Controls were also prepared without the template. Next, initiator AIBN was added in low light conditions, and the solutions were allowed to equilibrate for 12 hours in darkness. This step allowed the monomers and template to orient themselves and reach their free energy minima, thus beginning the configurational imprinting at the molecular level. However, this step occurs very quickly such as on the order of minutes.

The solutions were then transferred to an MBRAUN Labmaster 130 1500/1000 Glovebox, which provides an inert nitrogenous and temperature-controlled atmosphere for free-radical photopolymerization. With an increase in photoinitiator wt. %, this step can proceed in air. The solutions were uncapped and left open to the nitrogen until the oxygen levels reached negligible levels (<0.1 ppm). The solutions were inserted into glass molds (6 in. by 6 in.) separated by a Teflon frame 0.8 mm wide, as measured by a Vernier caliper. The glass plates were coated with chlorotrimethylsilane in order to prevent the polymer matrix from sticking to the glass, as it demonstrates a strong adherent tendency due to hydrogen bonding. Polymerization was carried out for ten minutes at 325 V using a Dymax UV light source. The intensity of radiation was 40 mW/cm$^2$, as measured with a radiometer, and the temperature was 36° C., as measured by a thermocouple.

The polymer was peeled off the glass plates with flowing deionized water (Millipore, 18.2 mO·cm, pH 6), and then was allowed to soften for approximately 10 minutes. Circular discs were cut using a Size 10 cork borer (13.5 mm), and were typically washed for 5 days in a continuous flow system using deionized water. All washes proceeded until the absence of detectable drug was verified by spectroscopic monitoring. To obtain dry weights, some discs were allowed to dry under laboratory conditions (20° C.) for 36 hours. The discs were then transferred to a vacuum oven (27 in. Hg, 33-34° C.) for 48 hours until they were dry (less than 0.1 wt % difference).

Polymer penetrant uptake and swelling data were obtained in deionized water with samples taken every 5 min. for the first hour, and then every hour for 10 hours until equilibrium was reached. As the gel was removed from the water, excess surface water was dabbed with a dry Kim wipe. The equilibrium weight swelling ratio at time t, q, for a given gel was calculated using the weights of the gels at a time and the dry polymer weights, respectively, using equations based on Archimedes principle of buoyancy. Dynamic and Equilibrium Template Binding: Dynamic template drug molecule binding was performed until equilibrium had been established for each system. Stock solutions of drug with a concentration 2 mg/ml were prepared and diluted with deionized water to produce 0.1, 0.2, 0.3, 0.4 and 0.5 mg/ml solutions. Each solution was vortexed for 30 seconds to provide homogeneity, and initial UV absorbances were noted. Gels were then inserted into the vials and were placed on a Stovall Belly Button Orbital Shaker over the entire duration of the binding cycle to provide adequate mixing. A 200 μL aliquot of each sample was placed in a Corning Costar UV-transparent microplate, and absorbance readings were taken using a Biotek Spectrophotometer at 268 nm. After measurement, the reading sample was returned to the original samples, to avoid fluctuations in concentrations due to sampling methods.

Dynamic Release Studies: In obtaining the preliminary results, dynamic release studies were conducted in DI water, artificial lacrimal fluid (6.78 g/L NaCl, 2.18 g/L NaHCO$_3$, 1.38 g/L KCl, 0.084 g/L CaCl$_2$.2H$_2$O, pH 8), and lysozyme (1 mg/ml) in artificial lacrimal fluid. Gels which had been drug loaded were placed in 30 ml of DI water, and the solutions were continuously agitated with a Servodyne mixer (Cole Palmer Instrument Co.) at 120 rpm. Release of drug was monitored at 268 nm by drawing 200 μL of solution into a 96-well Corning Costar UV-transparent microplate, and measurements were taken in a Synergy UV-Vis Spectrophotometer (Biotek). Absorbances were recorded for three samples, averaged, and corrected by subtracting the relevant controls. Solutions were replaced after each reading. Separate studies were conducted to determine if infinite sink conditions existed and those conditions were matched throughout all experiments.

Polymerization Kinetics and Network Formation: Solutions were prepared with 0, 0.1, 0.5, and 1 mole percent of Ketotifen in the initial monomer solutions. Kinetic studies were conducted with a differential scanning photocalorimeter (DPC, Model No. DSC Q100, TA Instruments with Mercury light source). Samples of 10 μL were placed in an aluminum hermetic pan and purged with nitrogen (flow rate 40 ml/min) in order to prevent oxidative inhibition. They were allowed to equilibrate at 35° C. for 15 minutes, before shining UV light at 40 mW/cm2 for 12 minutes.

The heat that evolved was measured as a function of time, and the theoretical enthalpy of the monomer solution was used to calculate the rate of polymerization, Rp, in units of fractional double bond conversion per second. Integration of the rate of polymerization curve versus time yielded the conversion as a function of time or reaction rate. The presence of template and a solvent, if used, was accounted for in the calculations, as it did not participate in the polymerization reaction. Experimental results were reproducible and the greatest source of error involved the assumed theoretical enthalpies in the calculations of the rate of polymerization and conversion. For all studies, the enthalpies were assumed to have errors of +5%. The assumptions in the copolymerization of two monomers (i.e., functional and cross-linking monomers) were that each monomer had equal reactivity and the theoretical enthalpy derived for a co-monomer mixture was an average of the enthalpies of individual monomers. The theoretical enthalpy of methacrylate double bonds was equal to 13.1 kcal mole-1 and the theoretical enthalpy of acrylate double bonds was equal to 20.6 kcal mole-1.

Results

Figure 5A:
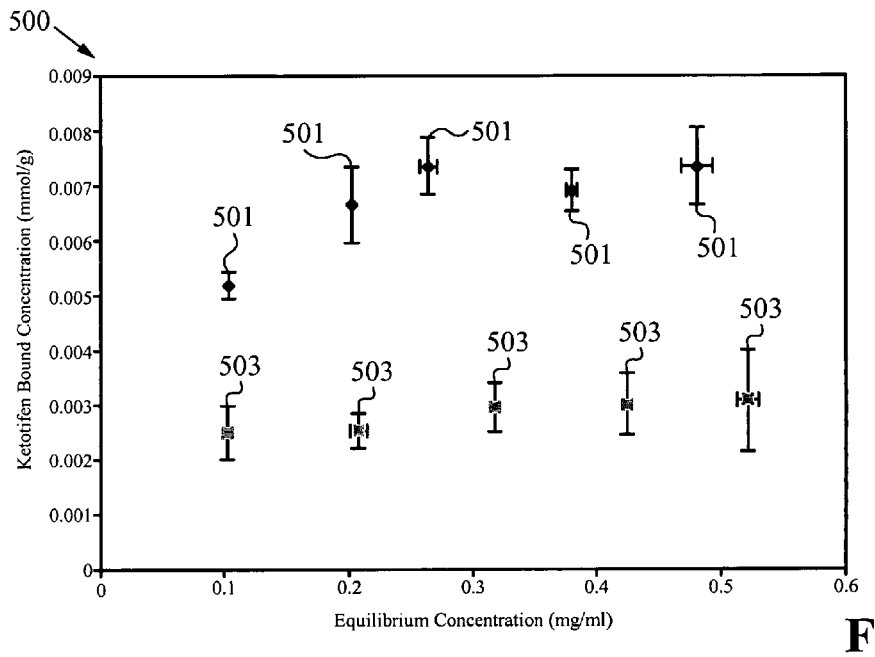
FIGS. 5A-B are graphs that compare Ketotifen equilibrium isotherms in water for a recognitive polymeric hydrogel and a control hydrogel.

FIG. 5A shows a graph 500 of the equilibrium binding isotherm for Ketotifen in water for Poly(acrylamide-co-HEMA-co-poly(ethylene glycol)200 dimethacrylate)hydrogel networks with a cross-linking percentage of 5%. N=3 and T=25° C. The recognitive hydrogel network is represented by the line 501 and the control hydrogel network is represented by the line 503. Percentage denotes percent mole crosslinker per mole total monomers in feed.

Figure 5B:
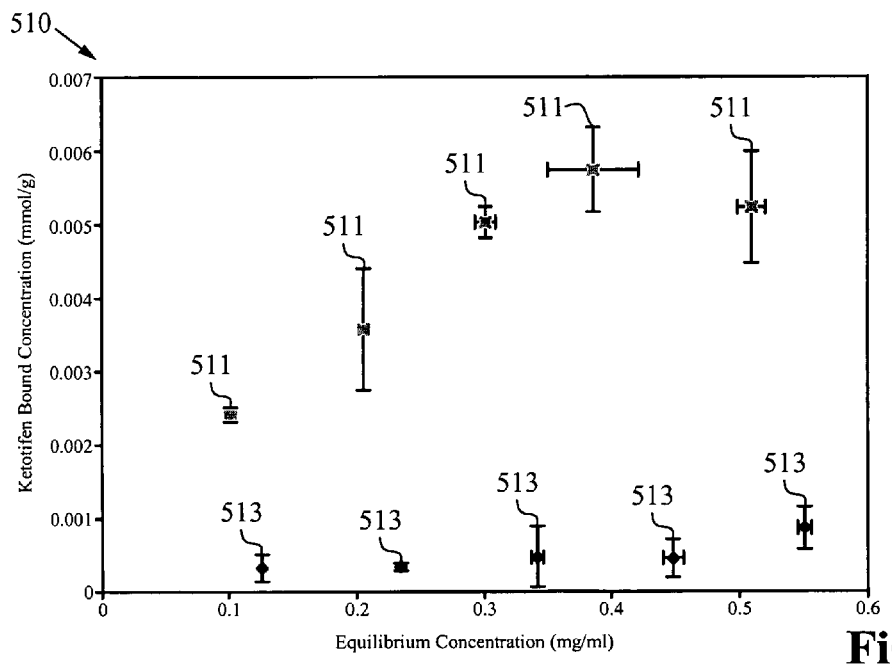

FIG. 5B shows a graph 510 of the equilibrium binding isotherm for Ketotifen in water for Poly(acrylic acid-co-HEMA-co-poly(ethylene glycol)200 dimethacrylate) hydrogel networks with a cross-linking percentage of 5%. N=3 and T=25° C. The recognitive hydrogel networks is represented by line 511 and the control hydrogel network is represented by line 513. Percentage denotes percent mole crosslinker per mole total monomers in feed.

Figure 5C:
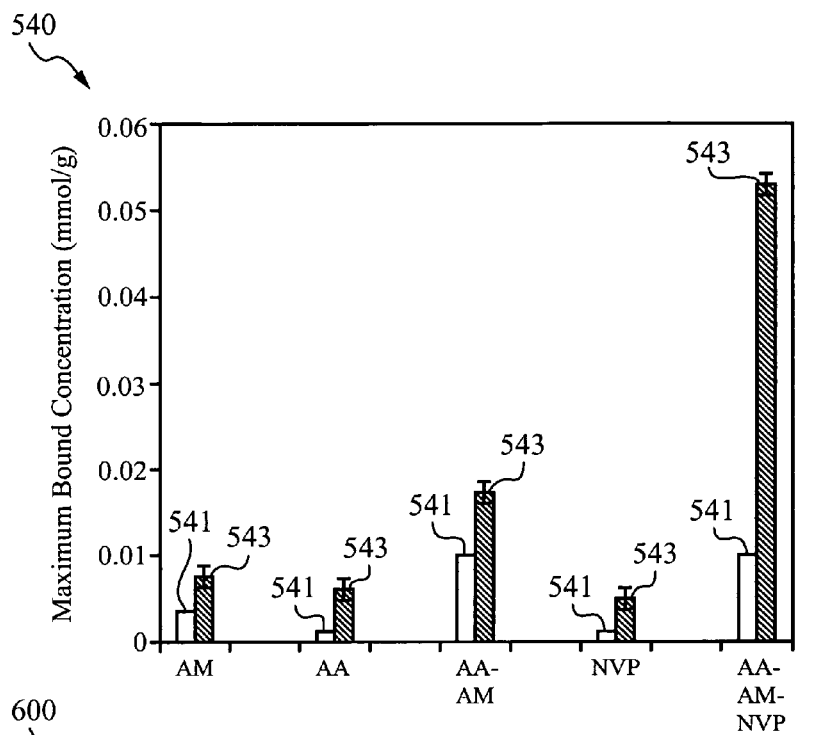
FIG. 5C graphs drug loading for recognitive polymeric hydrogels of the present invention against control hydrogels to show the enhanced drug loading for recognitive polymeric hydrogels of the present invention.

FIG. 5C shows a graph 540 of enhanced Loading of Ketotifen for Multiple Monomer Gels for Poly(n-co-HEMA-co-poly(ethylene glycol)200 dimethacrylate) Networks. The Functional monomers uses are acrylic acid, acrylamide, NVP, or an equal mole mixture of both. The Recognitive networks are shown as hatched bars 543 and the Control networks are shown as clear bars 541.

Figure 6:
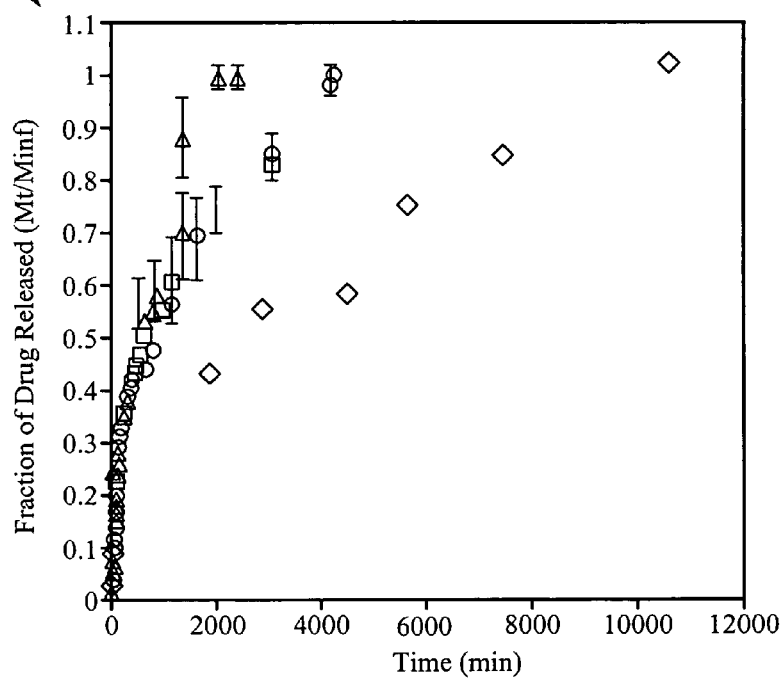
FIG. 6 shows a graph of drug release profiles for therapeutic contact lenses, in accordance with the embodiments of the invention.

FIG. 6 shows a graph 600 of Tailorable Release Profiles Of Therapeutic Contact Lenses for Poly(n-co-HEMA-co-poly (ethylene glycol)200 dimethacrylate) Networks in Artificial Lacrimal Fluid, where n is AM (represented by circles), AA (represented by squares), AA-AM (represented by triangles), and NVP-AA-AM (represented by diamonds) recognitive networks respectively. Results demonstrate approximately constant release rate of ketotifen fumarate for 1 to 5 days.

Figure 7A:
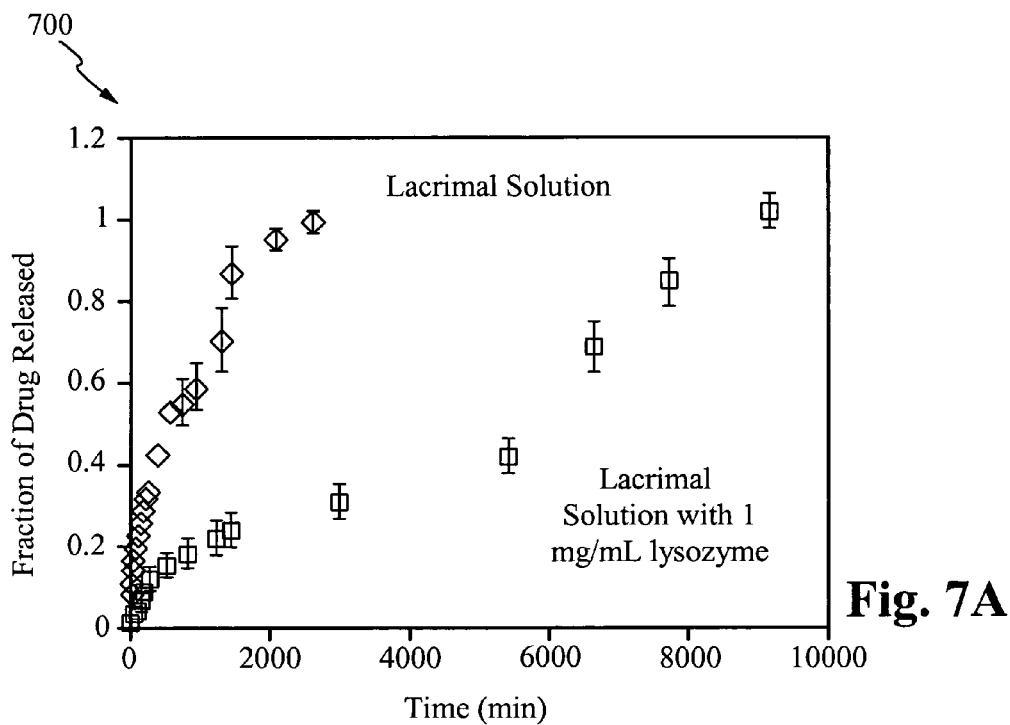
FIG. 7A-B show graphs of drug release profiles for recognitive polymeric hydrogels, in accordance with the embodiments of the invention

FIG. 7A shows a graph 700 of Release Data for Poly(AM-co-HEMA-co-poly(ethyleneglycol)200 dimethacrylate) Recognitive Networks. Fraction of Mass Released in Artificial Lacrimal Solution With/Without Lysozyme.

Figure 7B:
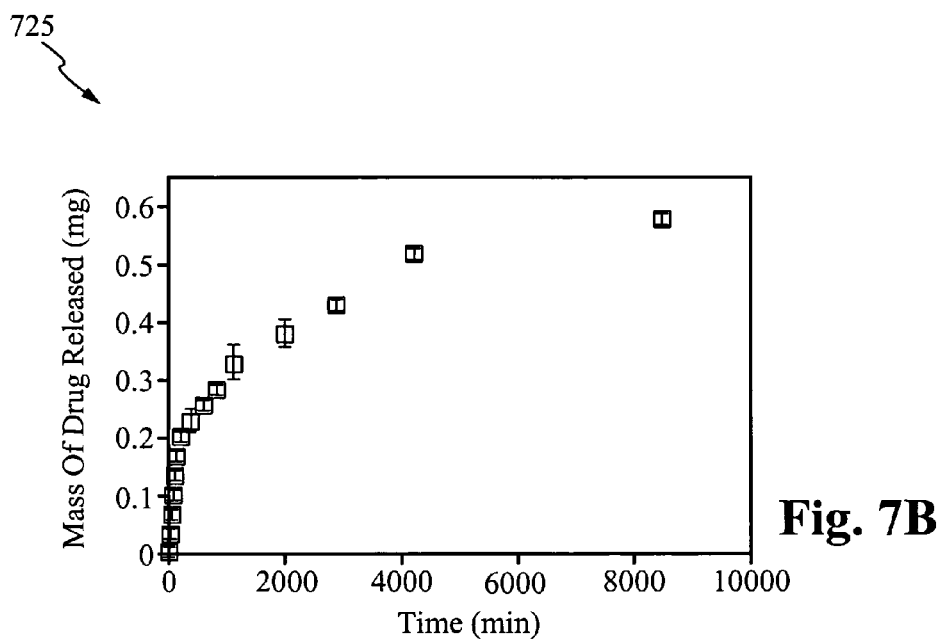

FIG. 7B shows a graph 725 of Release Data for Poly(AM-co-AA-co-HEMA-co-poly(ethyleneglycol)200 dimethacrylate) Networks Mass of Drug Released in Artificial Lacrimal Solution.

I. Enhanced Loading and Performance of Multiple Monomer Mixtures

In the preliminary work, hydrogels were produced with enhanced loading for ketotifen fumarate. Polymers were made with the following monomers: acrylic acid (AA), N-vinyl 2-pyrrolidone (NVP), acrylamide (AM), 2-hydroxyethylmethacrylate (HEMA), and polyethylene glycol (200) dimethacrylate (PEG200DMA).

We hypothesized that gels composed of multiple functional monomers would outperform those composed of single functional monomers. For anti-histamine recognitive polymers, this would better mimic the docking site of histamine at the molecular level providing all the relevant functionality necessary for non-covalent interactions. We have proved that loading properties of gels are improved with multiple monomer mixtures.

Gels of multiple complexation points with varying functionalities outperformed the gels formed with less diverse functional monomer and showed the highest maximum bound of ketotifen and highest difference over control gels. Equilibrium binding isotherms for Poly(AM-co-AA-co-HEMA-co-PEG200DMA) networks demonstrate enhanced loading with a factor of 2 times increase in the loading of drug compared to conventional networks (i.e., gels prepared without template and comparable to existing contact lenses) depending on polymer formulation and polymerization conditions. Poly(AM-co-HEMA-co-PEG200DMA) networks demonstrated a factor of 2 or 100% increase in the loading of drug compared to control networks with lower bound amounts. Poly(AA-co-HEMA-co-PEG200DMA) networks show a factor of 6 times increase over control in the loading of ketotifen with the overall drug bound being the lowest of the polymer formuations studies (approximately 33% less ketotifen loading than the AM functionalized network).

For all systems, an increase in the amount of loaded drug has been confirmed, but with the most biomimetic formulation (Poly(AA-co-AM-co-NVP-co-HEMA-PEG200DMA)) a significant increase in loading is demonstrated yielding the greatest loading potential (the highest loading achieved to date and 6× over control networks due to multiple binding points with varying functionalities) (FIG. 5C).

II. Dynamic Drug Release Profiles

Dynamic release profiles in artificial lacrimal solution and an artificial lacrimal solution with protein, demonstrated extended release of a viable therapeutic concentration of ketotifen. Release studies confirmed that release rates can be tailored via type and amount of functionality and extended from one to five days. FIG. 6 highlights normalized data of the fraction of drug released versus time (mass delivered at time t divided by the mass delivered at infinite time). For poly(n-co-HEMA-co-PEG200DMA) networks (where n was AA-co-AM, AM, or AA), the release of drug showed a relatively constant rate of release for approximately 1 day, with little difference in the release profile. However, the most structurally biomimetic network, poly(AA-co-AM-co-NVP-co-HEMA-PEG200DMA), exhibited a five fold increase in the extended release profile (i.e., approximately 5 days).

It is hypothesized that providing all the relevant functionality to the mimicked docking site with the proposed polymer synthesis technique affords a higher affinity of the drug for the network and thus an even slower release of drug compared to control networks. Furthermore, a five to seven day release profile fits quite well into the time usage of one-week extended-wear soft contacts.

It has been demonstrated that the loading of drug can be controlled by the type, number, and diversity of functionality within the network. The loading (and hence the mass delivered) can also be controlled by the initial loading concentration of the drug. We have demonstrated control over the cumulative mass of drug released by changing the loading concentration. By considering the relative size of our gels (i.e., gels were slightly bigger than normal lenses) and mass of drug released in comparison to typical ophthalmic eye drop dosages (ketotifen 0.25 mg/mL of solution with one drop every 8 hours), the preliminary results revealed that a therapeutically relevant dosage could be delivered for extended periods of time.

To investigate the effect of protein on dynamic release, we chose lysozyme as a model protein since it is the largest protein component in tear fluid. FIGS. 7A-B highlights the poly(AM-co-HEMA-co-PEG200DMA) network release profile in artificial lacrimal solution with lysozyme, which leads to a factor of 5 increase in the duration of release. For the most structurally biomimetic network, poly(AA-co-AM-co-NVP-co-HEMA-PEG200DMA), this could lead to a sustained release approaching 25 days. These studies demonstrate that the time of release may be delayed even further in an in vivo environment, leading to a substantial increase in applicability of contact lens ocular delivery.

III. Polymerization Reaction Analysis

The rate of polymerization for a given conversion decreased for increasing mole percentage of template molecule in pre-polymerization monomer solution. Thus, the formation of polymer chains and the enhanced loading due to the configurational biomimetic effect may be related to the propagation of polymer chains. The template molecule poses physical constraints to free radical and propagating chain motion and hence effectively lowers the rate of polymerization in the creation of ligand binding pockets. These results show that CBIP is reflected at the molecular level. For a given conversion, the rate of polymerization was lower for the multiple functional monomer pre-polymerization mixtures than the single monomer mixtures. We hypothesize that CBIP with multiple monomers results in the formation of better ligand-binding pockets with enhanced loading properties which leads to slower rates of polymerization.

IV Equilibrium Swelling Profiles and Mechanical Property Analysis:

Equilibrium swelling studies in DI water and 0.5 mg/ml concentrated ketotifen solution) indicated that recognitive and control networks were statistically the same and that 40% of the swollen gels is water, which indicates that the comfort of wearing and oxygen permeability of these gels is in agreement with conventional contact lenses. These studies indicated that CBIP, and not an increased porosity or surface area of the gel, is responsible for the enhanced loading properties. It also demonstrated that the loading process does not affect the rate of swelling of the polymer matrix.

Further studies on the mechanical properties of the gels have shown comparable storage and loss moduli, glass transition temperatures and damping factors to that of conventional contact lenses (data not shown). Each gel produced was optically clear and had sufficient viscoelasticity to be molded in thin films (for refractive differences)

CONCLUSION

Polymerization kinetics in the presence of the template reveal mechanisms of interaction as well as provide criteria with which other template-monomer systems can be chosen experimentally. The use of a biomimetic approach for synthesizing recognitive hydrogel polymers has led to the development of an ophthalmic drug delivery system using contact lenses formed from the recognitive hydrogel polymer. The ophthalmic drug delivery system of the present invention can provide improved bioavailability and efficacy of drug delivery and exhibit controlled time release of the drug. The ophthalmic drug delivery system can be tailored to exhibit properties suitable for the intended drug therapy and has a potential to replace traditional eye drop therapies and other methods.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiment chosen for illustration without departing from the spirit and scope of the invention. Specifically, it will be apparent to one of ordinary skill in the art that the device of the present invention could be implemented in several different ways and the apparatus disclosed above is only illustrative of the preferred embodiment of the invention and is in no way a limitation.

What is claimed is:

1. A method for making a drug delivery system, the method comprising:
   a) forming a weakly cross-linked polymeric hydrogel having between about 0.1% to 20% moles cross-linking monomer and/or macromer species per total moles of all monomer and/or macromer species present, wherein forming the polymeric hydrogel comprises: forming a solution comprising amounts of bio-template, wherein the bio-template is a drug, a functionalized monomer and a cross-linking monomer; complexing the functionalized monomer and the bio-template in the solution through non-covalent interactions; and initiating copolymerization of the functionalized monomer and the cross-linking monomer;
   b) forming the weakly cross-linked polymeric hydrogel into contact lens;
   c) identifying receptor sites at a target biological tissue that are associated with a biological mechanism of a drug at the target biological tissue; and
   d) synthesizing the functionalized monomer with functional groups that mimic the receptor sites of the target biological tissue to form a matrix for selectively binding the drug of the bio-template and the functionalized monomer to promote the controlled, time release of the drug.

2. A method for making a drug delivery system, the method comprising:
   a) forming a weakly cross-linked polymeric hydrogel having between about 0.1% to 20% moles cross-linking monomer and/or macromer species per total moles of all monomer and/or macromer species present, wherein forming the polymeric hydrogel comprises: forming a solution comprising amounts of bio-template, a functionalized monomer and a cross-linking monomer; complexing the functionalized monomer and the bio-template in the solution through non-covalent interactions; and initiating copolymerization of the functionalized monomer and the cross-linking monomer;
   b) forming the weakly cross-linked polymeric hydrogel into contact lens;
   c) identifying receptor sites at a target biological tissue that are associated with a biological mechanism of a drug at the target biological tissue;
   d) synthesizing the functionalized monomer with functional groups that mimic the receptor sites of the target biological tissue to form a matrix for selectively binding the drug on the functionalized monomer within the polymeric hydrogel; and
   loading the contact lens with the drug, wherein the drug complexes with the functionalized monomer as a result of the monomer having the functional groups mimicking the receptor sites at the biological tissue wherein the drug is identified as having a biological mechanism of action.

3. The method of claim 1, further comprising washing a portion of the bio-template from the weakly cross-linked polymeric hydrogel and loading the recognitive polymeric hydrogel with a drug.

4. The method of claim 3, wherein the drug is selected from the group consisting of an antibiotic, an anti-inflammatory, an antihistamine, an antiviral agent, a cancer drug, an anesthetic, a cycloplegic, a mydriatics, a lubricant agent, a decongestant, a vasoconstrictor, a vasodilator, an immuno-suppressant, an immuno-modulating agent, an anti-glaucoma agent, anti-infective, hyperosmolar agent, vitamins, growth factors, growth factor antagonists, sympathomimetics, an adrenergic agonist, an anti-cataract agent, an anti-hypertensive agent, an anti-macular degeneration agent, an ocular permeation enhancing agent, an anti-retinal disease agent, an anti-retinitis pigmentosa agent, an anti-diabetic retinopathy agent and an ocular diagnostic agent.

5. The method of claim 1, further comprising washing a portion of the bio-template from the contact lenses and loading the contact lenses with a drug by soaking the contact lenses in an aqueous drug solution.

6. The method of claim 5, wherein the drug is selected from the group consisting of an antibiotic, an anti-inflammatory, an antihistamine, an antiviral agent, a cancer drug, an anesthetic, a cycloplegic, a mydriatics, a lubricant agent, a decongestant, a vasoconstrictor, a vasodilator, an immuno-suppressant, an immuno-modulating agent, an anti-glaucoma agent, anti-infective, hyperosmolar agent, vitamins, growth factors, growth factor antagonists, sympathomimetics, an adrenergic agonist, an anti-cataract agent, an anti-hypertensive agent, an anti-macular degeneration agent, an ocular permeation enhancing agent, an anti-retinal disease agent, an anti-retinitis pigmentosa agent, an anti-diabetic retinopathy agent and an ocular diagnostic agent.

7. The method of claim 1, wherein the drug is selected from the group consisting of an antibiotic, an anti-inflammatory, an antihistamine, an antiviral agent, a cancer drug, an anesthetic, a cycloplegic, a mydriatics, a lubricant agent, a decongestant, a vasoconstrictor, a vasodilator, an immuno-suppressant, an immuno-modulating agent, an anti-glaucoma agent, anti-infective, hyperosmolar agent, vitamins, growth factors, growth factor antagonists, sympathomimetics, an adrenergic agonist, an anti-cataract agent, an anti-hypertensive agent, an anti-macular degeneration agent, an ocular permeation enhancing agent, an anti-retinal disease agent, an anti-retinitis pigmentosa agent, an anti-diabetic retinopathy agent and an ocular diagnostic agent.

8. The method of claim 3, wherein the drug is ketotifen.

9. The method of claim 1, wherein the formation of the weakly cross-linked polymeric hydrogel comprises forming a solution in the absence of a solvent.

10. A method for making a drug delivery system, the method comprising:
    a) forming a weakly cross-linked polymeric hydrogel having between about 0.1% to 20% moles cross-linking monomer and/or macromer species per total moles of all monomer and/or macromer species present, wherein forming the polymeric hydrogel comprises: forming a solution in the absence of a solvent comprising amounts of bio-template, a functionalized monomer and a cross-linking monomer; complexing the functionalized monomer and the bio-template in the solution; and initiating copolymerization of the functionalized monomer and the cross-linking monomer;

b) forming the weakly cross-linked polymeric hydrogel into contact lenses;
c) identifying receptor sites at a target biological tissues that are associated with a biological mechanism of a drug at the target biological tissue;
d) synthesizing the functionalized monomer with functional groups that mimic the receptor sites of the target biological tissue to form a matrix for selectively binding the drug on the functionalized monomer within the polymeric hydrogel, wherein the functionalized monomer is configured to non-covalently complex with the bio-template; and
e) loading the contact lens with the drug, wherein the drug complexes with the functionalized monomer as a result of the monomer having the functional groups mimicking the receptor sites at the biological tissue wherein the drug is identified as having a biological mechanism of action.

* * * * *